(12) United States Patent
Boileau et al.

(10) Patent No.: US 10,736,767 B2
(45) Date of Patent: Aug. 11, 2020

(54) UPPER EXTREMITY BRACES

(71) Applicants: Pascal Boileau, Nice (FR); Jean Christophe Bouletrean, Nice (FR)

(72) Inventors: Pascal Boileau, Nice (FR); Jean Christophe Bouletrean, Nice (FR)

(*) Notice: Subject to any disclaimer, the term of this patent is extended or adjusted under 35 U.S.C. 154(b) by 927 days.

(21) Appl. No.: 15/192,617

(22) Filed: Jun. 24, 2016

(65) Prior Publication Data
US 2017/0027737 A1 Feb. 2, 2017

(30) Foreign Application Priority Data

Jun. 25, 2015 (EP) .................................... 15306005

(51) Int. Cl.
A61F 5/00 (2006.01)
A61F 5/37 (2006.01)
A61F 5/01 (2006.01)

(52) U.S. Cl.
CPC .......... A61F 5/3738 (2013.01); A61F 5/0118 (2013.01); A61F 5/3723 (2013.01); A61F 5/3753 (2013.01)

(58) Field of Classification Search
CPC ........ A61F 5/37; A61F 5/3723; A61F 5/3738; A61F 5/3753
USPC ............................... 602/4; 128/882; D24/190
See application file for complete search history.

(56) References Cited

U.S. PATENT DOCUMENTS

| | | | | |
|---|---|---|---|---|
| 114,615 A * | 5/1871 | Smitley | ................. | A61F 5/3738 602/4 |
| 3,780,729 A * | 12/1973 | Garnett | ................. | A61F 5/3738 602/4 |
| 4,487,199 A * | 12/1984 | Saringer | ............... | A61F 5/3738 601/33 |
| 4,497,316 A * | 2/1985 | Lilla | ..................... | A61F 5/3738 602/4 |
| 4,598,702 A * | 7/1986 | Lilla | ..................... | A61F 5/3738 602/4 |
| 5,385,536 A * | 1/1995 | Burkhead | ............. | A61F 5/3753 2/45 |
| 5,407,420 A * | 4/1995 | Bastyr | ..................... | A61F 5/013 602/16 |
| 5,665,058 A * | 9/1997 | Young | .................. | A61F 5/3753 602/16 |

(Continued)

FOREIGN PATENT DOCUMENTS

| | | |
|---|---|---|
| DE | 20116743 | 1/2002 |
| EP | 1013248 | 6/2000 |

Primary Examiner — Kim M Lewis

(74) Attorney, Agent, or Firm — J. Wiley Horton

(57) ABSTRACT

A brace for restricting the movement of a shoulder joint, the brace including a trunk module attachable to a human body, wherein the trunk module includes a strap for attaching the brace to the body; and at least one first part of a locking mechanism; a forearm module pivotable relative to the trunk module, the forearm module further including a second part of a locking mechanism capable of engaging and disengaging with the at least one first part of the locking mechanism; and a posterior upper arm support attached to the trunk module in a fixed position; wherein in a first orientation the at least one first part of the locking mechanism is engaged with the second part of the locking mechanism; and wherein in a second orientation the at least one first part of the locking mechanism is disengaged from the second part of the locking mechanism.

13 Claims, 6 Drawing Sheets

(56) References Cited

U.S. PATENT DOCUMENTS

| | | | | |
|---|---|---|---|---|
| 7,563,236 | B2* | 7/2009 | Kazmierczak | A61F 5/3753 |
| | | | | 602/4 |
| 8,109,273 | B2* | 2/2012 | Golden | A41D 13/00 |
| | | | | 128/878 |
| 8,273,041 | B2* | 9/2012 | Goumas | A61F 5/3738 |
| | | | | 128/845 |
| 8,454,544 | B2* | 6/2013 | Barnes | A61F 5/3723 |
| | | | | 602/19 |
| 9,827,133 | B1* | 11/2017 | Krenzel | A61F 5/3738 |
| 2009/0192424 | A1* | 7/2009 | Choudhury | A61F 5/3746 |
| | | | | 602/4 |
| 2010/0152635 | A1* | 6/2010 | Borden | A61F 5/3738 |
| | | | | 602/4 |
| 2012/0245498 | A1* | 9/2012 | Krenzel | A61F 5/3738 |
| | | | | 602/4 |
| 2013/0317401 | A1* | 11/2013 | Joslin | A61F 5/3738 |
| | | | | 602/4 |
| 2014/0194798 | A1* | 7/2014 | Sotereanos | A61F 5/0118 |
| | | | | 602/4 |
| 2014/0221888 | A1* | 8/2014 | Benenati | A61F 5/3753 |
| | | | | 602/4 |
| 2014/0371644 | A1* | 12/2014 | Erbe | A61F 5/013 |
| | | | | 602/4 |

* cited by examiner

UPPER EXTREMITY BRACES

CROSS-REFERENCE TO RELATED APPLICATIONS

This patent application claims priority to European patent application number 15306005.8 filed Jun. 25, 2015 and entitled "Improvements in or relating to upper extremity braces." The subject matter of patent application number 15306005.8 is hereby incorporated by reference in its entirety.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

BACKGROUND

It is known to use a brace or splint to support a joint which has undergone either an operation, been injured or is the subject of a long existing medical condition. Different joints require different braces to support the joint, each being adapted accordingly. Braces can be used on both the upper and lower extremities of the human body. One joint which is particularly susceptible to injury and problems, and which often requires surgery, is the shoulder. The shoulder is a complex joint with many bones, tendons, muscles and the like. After injury or surgery, it is often necessary to immobilize the shoulder to avoid or restrict movement and in turn aid the healing process.

Current existing braces for shoulders are cumbersome and give rise to a number of problems both from a practical point of view and a medical point of view. Typically shoulder braces are adapted to maintain the shoulder in a fixed position by strapping the arm in some way to the body by means of straps, belts, suspenders, and the like. The position of the arm relative to the body will depend upon the type of problem the patient has. In some cases the forearm will be across the body, in other cases the forearm will be extended upwards and in other situations the forearm may extend horizontally from the body in line with the shoulder. Typical types of existing braces are shown in FIG. 1.

Some of the problems associated with the existing braces are discussed below. One problem with existing braces is that they are very complicated to use. It is very difficult if not impossible for the patient to put on or remove the brace alone and help is generally required to position the brace correctly.

It is also difficult to find a brace that fits all patients. This generally means there are different braces for different sized people. As a result it is necessary to have a number of different sized braces, this adds to the costs of the design and manufacture and means that the hospital or doctor's surgeries need to stock many braces of different sizes.

Most of the existing braces completely immobilize the upper limb (as required) and the forearm tends to be confined within a portion of the brace, which completely captures the forearm by means of a circumferential tube with straps. The elbow joint is typically maintained at about 90° and the forearm is restricted and practically unable to move. This can lead to a number of problems such as elbow stiffness, stagnation of edema and hematoma, swelling, paresthesia, vein thrombosis and the like. In addition, compartment syndrome in the forearm may occur. The fact that the upper limb is rigidly held in a fixed position may also be detrimental to future joint function and may result in tissue atrophy. In most existing braces there are straps which go round the neck and the back the patient and can cause chafing of the skin and in some cases the sensation of strangulation.

If the patient were to attempt to extend the elbow and straighten the arm, any such movement would typically bring about a forward projection of the shoulder. This can provide a source of pain by tensioning the soft tissue and disturbing any bone fracture fragments being repaired. If this occurs in the early stages of recuperation, when lying down, the reattachment sutures can be compromised and the tendons and ligaments may become detached. This is particularly the case for surgery to repair the rotator cuff, Bankart lesions or osteosynthesis. It should be noted that the current braces do not provide the facility for the patients' to move the elbow, but trying to do so inadvertently can result in the problem identified above.

Due to the nature of existing braces, patients often find sleeping difficult and uncomfortable. With the elbow at 90° flexion in most situations, the hand extends upwards when the patient is sleeping. This can lead to numbness and lack of blood flow in the hands and lower arm. In addition, the elbow and wrist can become stiff due to lack of movement.

Most existing shoulder braces immobilize the shoulder's internal rotation, which may causes harmful consequences to the tendons and ligaments and bones as highlighted below.

For healing tendons of the rotator cuff, the arm position adopted using existing shoulder braces typically does not match the natural rest position or the muscular balance and tendon positions of the shoulder. This gives rise to tensioning of the external rotator muscles and shrinkage of the internal rotator muscles and the rotator interval.

For healing the lesions of the labrum and glenohumeral ligaments in the case of anterior and posterior shoulder instability, immobilization in internal rotation may cause medial scarring of the labrum, which is a recurrent source of anterior instability of the shoulder. Conversely, the neutral rotation or external rotation works in favor of closing the Bankart separation and the healing of the labrum is in a good position.

For healing fractures of the proximal humerus, immobilization of internal rotation of the shoulder after a fracture of the proximal humerus leads to consolidation in a faulty position: for instance malunion in the internal rotation in diaphyseal fractures of the surgical neck and tuberosity malunion in fractures having 3 or 4 fragments can lead to posteromedial migration of the tochiter and anteromedial migration of the lesser tuberosity.

SUMMARY

A brace for supporting the forearm and for restricting movement of one of more joint is provided. This Summary is provided to introduce a selection of disclosed concepts in a simplified form that are further described below in the Detailed Description including the drawings provided. This Summary is not intended to identify key features or essential features of the claimed subject matter. Nor is this Summary intended to be used to limit the claimed subject matter's scope.

An object of the present invention is to seek to solve at least some problems presented above. In addition, it is an object of the present invention to enable the shoulder to be immobilized in a position of neutral rotation of the shoulder with about 90° flexion of the elbow and also to allow easy mobilization of the shoulder, elbow and wrist as required, to avoid stiffness and retraction of the muscles and tendons, which can become irreversible. In addition, the neutral rotation aids recovery during rehabilitation.

A further object of the present invention is to provide a brace which allows the patient to sleep with their arm extended (in other words not at 90° flexion), without any detrimental mobilization of the shoulder.

In addition, it is an object of the present invention to provide a brace which can be easily put on and taken off by the patient without assistance from a third party.

BRIEF DESCRIPTION OF THE DRAWINGS

The accompanying drawings, which are incorporated in and constitute a part of this disclosure, illustrate various example embodiments. In the drawings.

DETAILED DESCRIPTION

Figure 1:
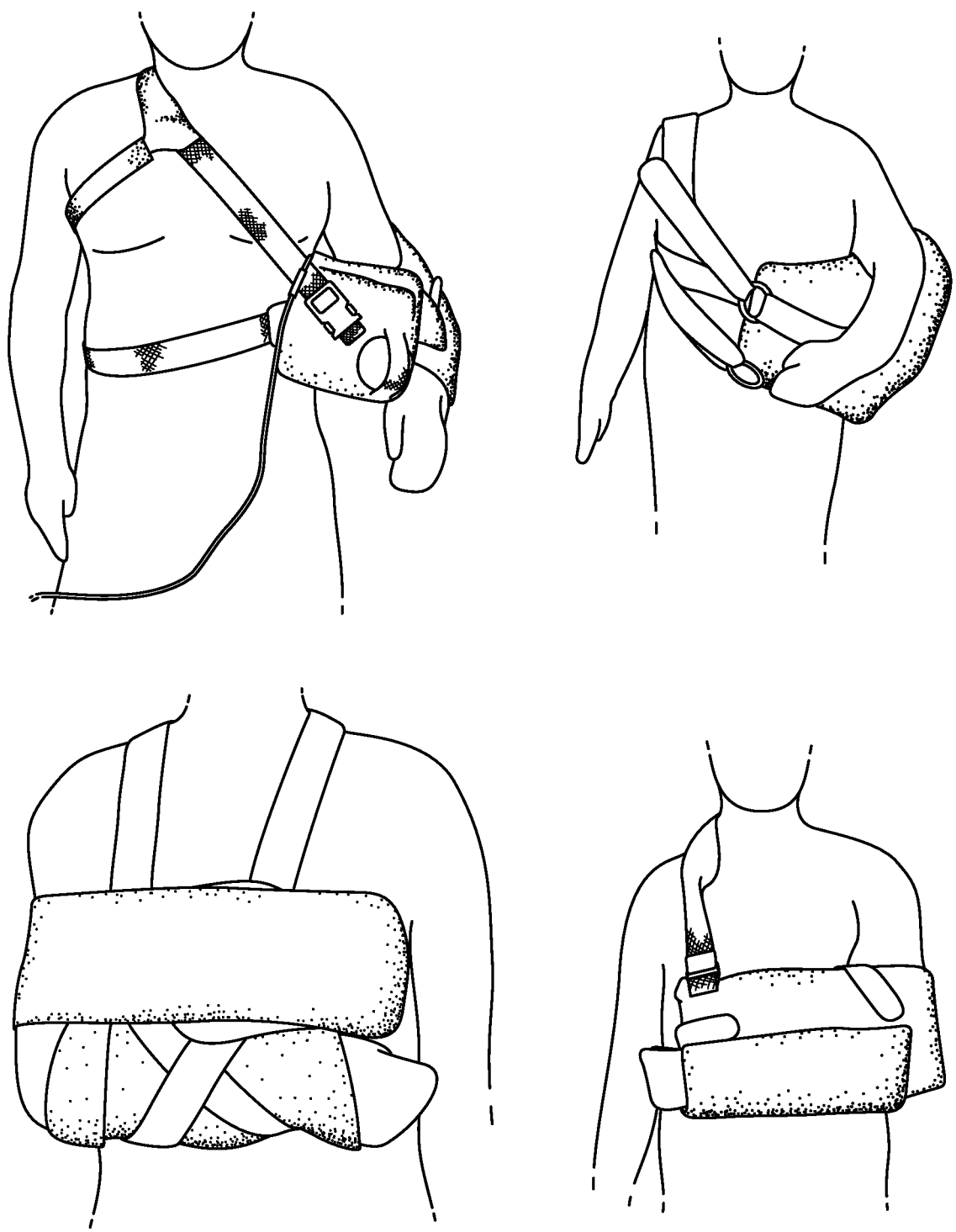
FIG. 1 is a drawing showing a number of existing braces, forming the prior art.

The following detailed description refers to the accompanying drawings. Wherever possible, the same reference numbers are used in the drawings and the following description to refer to the same or similar elements. While embodiments may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the invention. Instead, the proper scope of the invention is defined by the appended claims.

According to one aspect of the present invention, there is provided a brace for supporting the forearm and for restricting movement of one of more joint, the brace comprising:—a trunk module attachable to a human body in the vicinity of the torso at the side of the body corresponding to the arm to be supported, wherein the trunk module includes a strap for attaching the brace to the body; and at least one first part of a locking mechanism; —a forearm module pivotable relative to the trunk module and adapted to support the forearm in a plurality of positions relative to the upper arm, the forearm module further including at least one second part of a locking mechanism capable of engaging and disengaging with said first part of the locking mechanism; and —a posterior upper arm support attached to the brace in a fixed position to prevent movement of the upper arm and shoulder; wherein in a first orientation the at least one first part of the locking mechanism is engaged with the at least one second part of the locking mechanism such that forearm module is capable of positioning the forearm at first position relative to the upper arm; and wherein in a second orientation the at least one first part of the locking mechanism is disengaged from the at least one second part of the locking mechanism such that the forearm module is capable of pivoting relative to the trunk module to enable the forearm to be positioned at a second position relative to the upper arm.

Preferably the first and second part of the locking mechanism comprise a hook engageable with a notch.

In an embodiment the first position of the forearm relative to the upper arm is at an angle of about 90°.

Preferably the second position of the forearm relative to the upper arm is at an angle between about 90° and about 180°.

Preferably the trunk module further comprises a cushion for supporting the arm against body at a particular lateral displacement, based on the thickness of the cushion.

Preferably the trunk module further comprises an elasticated strap which passes round the body to hold the trunk module in the required position.

Preferably the elasticated strap includes a fixing for securing the elasticated strap.

Preferably the forearm module comprises a channel for supporting the forearm, wherein the channel includes an inner and outer edge and a curved-base portion.

Preferably the inner edge of the channel is higher than the outer edge of the channel.

In an embodiment one of the first or second part of the locking mechanism is located on the inner edge of the channel.

In an embodiment the trunk module includes connection plate on which one of the first or second part of the locking mechanism is located.

In an embodiment a pivot pin is located between the connection plate and the forearm module to allow the forearm module to pivot relative to the trunk module.

Preferably more than one first and second parts of the locking mechanism can enable the forearm to be secured in intermediate positions between about 90° and about 180° on engagement of different first and second parts.

Preferably the brace for allows movement of at least one of the shoulder, elbow, wrist or forearm.

According to a second aspect of the present invention there is provided a brace for supporting the forearm comprising a trunk module attachable to a human body in the vicinity of the torso at the side of the body corresponding to the arm to be supported and an arm support attached to the trunk module for supporting the arm in a predetermined position; wherein the trunk module comprises a cushion for supporting the arm against the body at a particular lateral displacement, based on the thickness of the cushion and a large elasticated strap which passes round the body to hold the trunk module in the required position.

According to a third aspect of the present invention there is provided a method of using the brace of the first and second aspects to support an arm.

According to a third aspect of the present invention there is provided a method of treatment using the brace of the first and second aspects to treat an arm.

Statements of invention to add once the claims are finalized.

In an embodiment, there is provided a brace restricting the movement of the shoulder and elbow joints with the following advantages:

a) A large belt or strap and a simple attachment system which allows the patient to put on and remove the brace alone (without the need of third party) keeping the patient autonomous and independent;

b) A pivoting system located at the elbow joint, which allows the patient to move the elbow joint in flexion-extension (when needed) without moving the shoulder joint. This allows:

extension of the elbow when sleeping at night while keeping the shoulder immobilized (in case of trauma or surgery of the shoulder);

mobilization the elbow to avoid stiffness during the day (in case of trauma or surgery of the elbow or of the shoulder);

c) A forearm module in the form of a half-tube, which leaves the forearm free (without being entrapped in a circumferential bag), to thereby allow:

reduction of any compression of the forearm;

the patient to remove the forearm from the forearm module to carry out self-rehabilitation with pendulum exercises and the like and then for the patient to be easily able to put the forearm back in the half tube and to put it back;

d) A pommel, which keeps the hand in a relaxed and functional position and allows the patient to squeeze a ball to improve blood circulation in the arm.

The present invention solves the problems of the prior art by providing a brace with an articulated elbow lock which enables immobilization of the joint when required, whilst providing the flexibility of being able to move the elbow in order to prevent stiffness and the other practical and medical problems highlighted above. The articulated elbow lock can be used, for example when the patient wishes to extend the arm so that it is straight, for example when sleeping or when carrying out physiotherapy exercises. The elbow can then be returned to 90° position when required.

The articulated elbow lock can be used to position the lower arm in different positions at different times to allow the lower arm to change position, without moving the shoulder in any detrimental way. The present invention also provides a brace which supports and positions the arm in the correct position without capturing the arm in a closable circumferential tube. In addition, the arrangement even allows the patient to be able to use their hand.

The open nature of the various elements of the new brace allows the patient to be less constrained but still supported as required. The patient can take off and put on the brace without help from a third party. The ability of the patient to ensure personal hygiene is also improved by the nature of brace according to the present invention. In addition, the risks of sweating and the resulting potential fungal inventions can be prevented.

Reference will now be made by way of example, to the accompanying drawings.

Figure 2A:
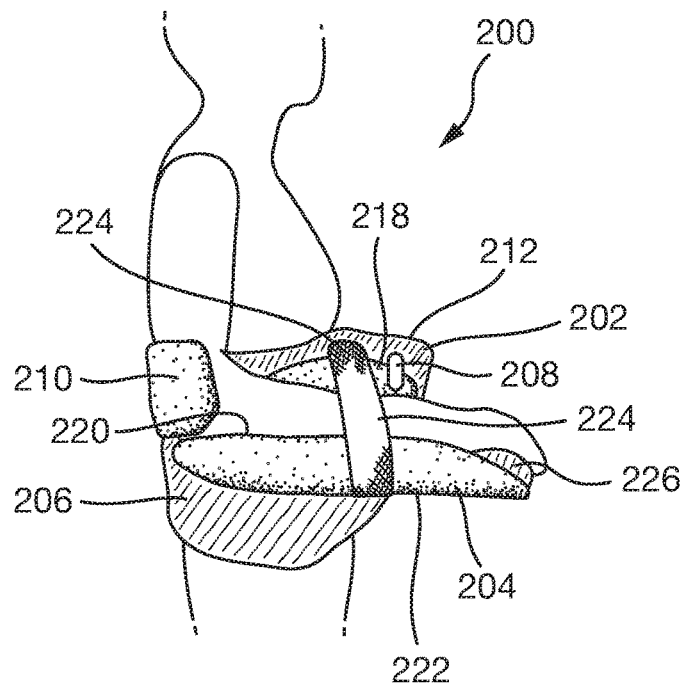
FIG. 2a is a schematic diagram showing a side view of a brace with the elbow at about 90° flexion, in accordance with an aspect of the present invention.
Figure 2B:
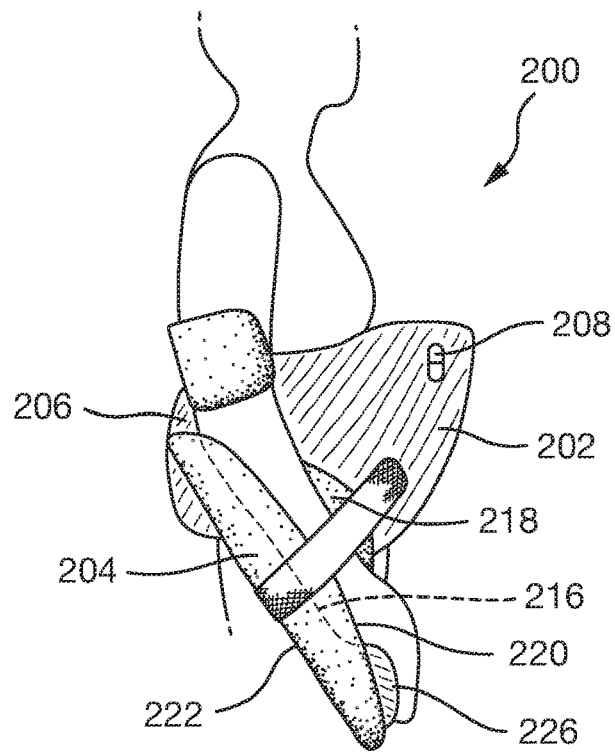
FIG. 2b is a schematic diagram showing a side view of a brace with the elbow extended, in accordance with an aspect of the present invention.

Referring to FIG. 2a, a schematic representation of a brace 200 is shown, in accordance with an embodiment of the present invention. In FIG. 2a the brace is shown with the elbow at about 90° flexion and in FIG. 2b the brace is shown with the elbow extended. At 90° flexion of the elbow, the forearm is held in a position of about 90° relative to the upper arm. With the elbow in an extended position the forearm is at an angle greater than about 90° and less than about 180° relative to the upper arm. The reference numbers for both FIG. 2a and FIG. 2b are the same. The description below relates to the position of the brace with the elbow at 90° flexion. It will be appreciated that the description applies equally to FIG. 2b.

The brace 200 includes a trunk module 202 and a forearm module 204. The trunk module and the forearm module are connected together by a connection plate shown generally at 206, which will be described in greater detail below.

The connection plate comprises an articulation allowing for freedom of movement in the sagittal plane. This enables flexion and extension of the elbow in a plane which passes from the anterior to the posterior of the body dividing the body into left and right half. The connection plate further includes a hook 208 which can hold the elbow in the 90° flexion position when engaged with the forearm module.

The brace also includes a posterior upper arm support 210 which is fixed relative to the brace on the trunk module by means of the connection plate, such that there is no movement of the upper part of the arm or the shoulder even when the lower part of the arm is extended. The posterior upper arm support is not connected to the forearm module. The posterior upper arm support is adapted to hold the upper arm in a fixed position and may include an open support as shown in FIG. 2a or may be closed by means of straps or other means. The posterior arm upper support may be made of a pliable material, such as aluminum or a thermoplastic, to enable shaping of the posterior upper arm support to fit the patient. Cushioning or equivalent soft materials may be incorporated into the internal surface of the posterior upper arm support for the comfort of the patient.

Figure 3:
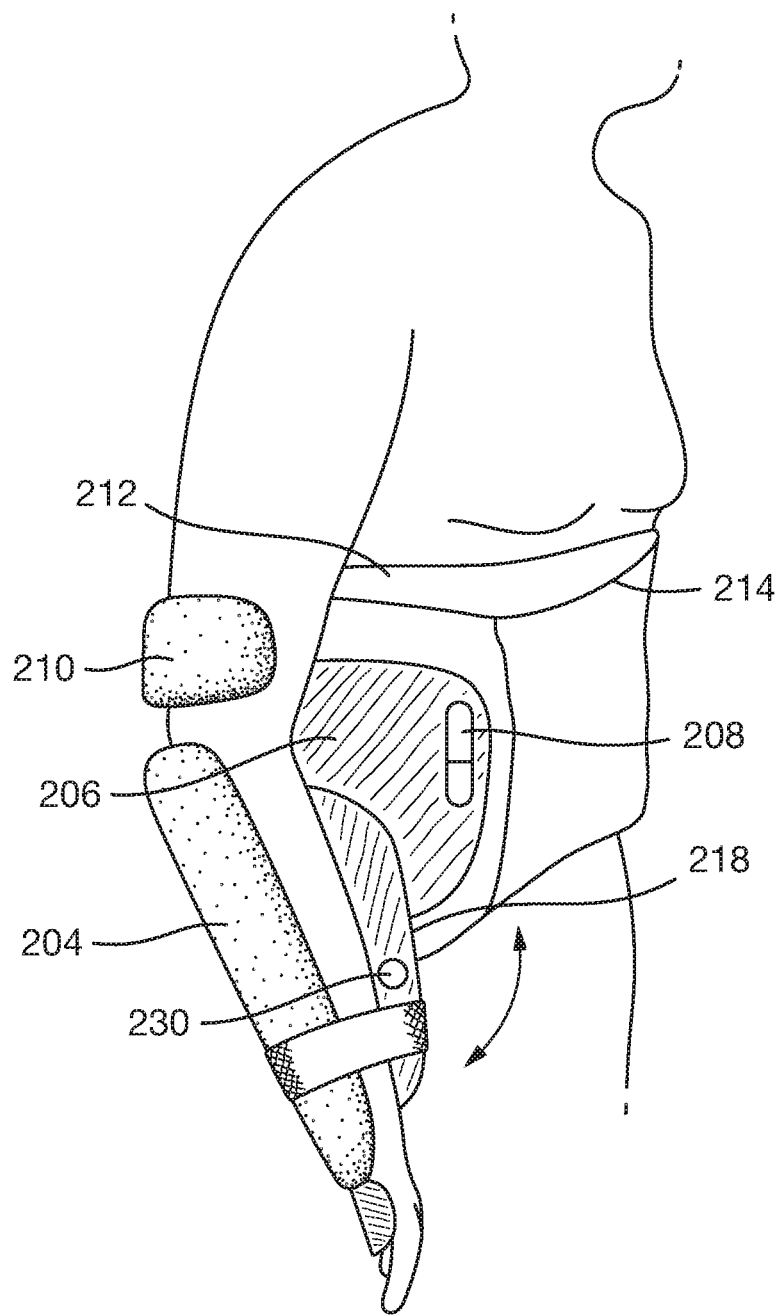
FIG. 3 is a schematic diagram of the elbow lock in an extended position, in accordance with an aspect of the present invention.

The trunk module comprises a cushion 212 and a fixing strap 214 (see FIG. 3). The cushion is typically crescent shaped and is positioned around the torso to the front and side of the patient. The cushion may be of foam or any other appropriate material or may be inflatable. The cushion may be of any thickness, depending on the amount of lateral displacement required for the arm relative to the body. Typically this may be about 20° abduction. If a greater, for example 46° to 60° or smaller abduction is required the cushion may be made bigger or smaller respectively. The cushion is designed such that it does not extend posteriorly (i.e. on the dorsal part of the torso) in order to avoid spine curvature and discomfort when the patient is lying down. When seen from the front the lower part of the cushion extends slightly downward on the hip so as to obtain a wide base which is comfortable when resting the arm in the forearm module (see FIG. 6). Seen from the side the front of the cushion is indented around the pubis to avoid contact with the legs when sitting down. The fixing strap is a wide elastic strap which wraps round the torso having hook-and-loop fittings to secure the strap.

The strap has a large width of between about 10 cm to 20 cm and is designed to be sufficiently wide to support the arm without the need of additional straps around the neck or any other attachments. This makes the brace significantly more comfortable for the patient to wear. The combination of a cushion and a large width strap provides a more comfortable brace, solving some of the discomfort issues of previously existing braces. In an alternative embodiment the strap can be in the form of a large belt, with appropriate fastenings. The strap is an integral part of the cushion and holds the whole brace in place. It may be necessary for larger patients, to employ an additional support, for example a shoulder strap, to help support the brace in position.

Both the cushion and fixing strap shown in the drawings can be adapted in many ways to fulfill the same function, as such the description above is not intended to limit the form, shape or make up of the cushion and fixing strap. The combination of the cushion and fixing strap may be used in conjunction with the brace according to the present invention or indeed in with other braces, even where elbow movement is restricted. The unique combination of the cushion and fixing strap addresses the problem of the patient being able to put the brace on by themselves. With the particular arrangement disclosed herein the patient can put on and take off the brace without help from other people. This gives much greater autonomy to the patient.

The forearm module includes a channel 216 for receiving the forearm. The channel is a thermoplastic molded or other malleable material and includes padding where required. The inner edge of the channel 216 (the edge in contact with the cushion of the trunk module) is higher than the outer edge of the channel 220 in order to keep the shoulder in a position of neutral rotation and to facilitate movement of the elbow as will be described in greater detail below. The channel further includes a curved base portion 222 for supporting the arm. The channel includes a strap 224 which can be attached by hook-and-loop or any other appropriate fixing. The strap extends from the inner edge to the outer edge of the channel to hold the forearm in place within the channel.

The forearm module further includes a removable and adjustable palm support 226 which can be adjusted in terms of length and inclination to correctly support the hand. The palm support may be fitted with padding and/or a ball (not shown) which the patient can squeeze to exercise the fingers. The length and inclination of the palm support relative to the channel can be adjusted according to the requirements of patient and can be changed by the patient to alleviate any tingling or other symptoms in the hand which cause discomfort to the patient. In an embodiment of the present invention, the palm support may be capable of being manipulated by the hand in order to give the opportunity to exercise the fingers without the need for a separate ball.

Referring to FIG. 3, the connection plate 206 is attached to the cushion and is juxtaposed to the forearm module. The connection plate is attached to the trunk module by means of a flat hook-and-loop system on a flat reinforced posterior section shown in FIG. 5, reference 232. The attachment of the cushion to the connecting plate can made by many other means, one such means being a magnetic system for example.

The forearm module 204 is fixed to the connection plate by means of the joint axis 228 which plays a dual role namely securing the connection plate to the front arm module and providing the joint axis of rotation for the forearm module relative to the trunk module (this will be described in more detail below).

In one embodiment the connection plate 206 and the forearm module 204 are a single unit that is secured to the trunk module by the hook-and-loop or magnetic system 232. This allows positioning the assembly of the connection plate 206 and the forearm module 204 according to each patient's arm length from the shoulder to the elbow and in turn ensures the location of the pivot point 228 is suitable for each patient.

The pivot pin 228 (see FIGS. 4a and 4b) is located in the region of the connection plate 206 and provides the joint axis of rotation for the forearm module relative to the trunk module (this will be described in more detail below).

The connection plate includes a hook 208 on the outer surface thereof, towards the front of the trunk module. The hook extends outwardly from the connection plate towards the forearm module and then upwards. The hook generally includes curved surfaces so that the hook cannot cause injure to the forearm. On the forearm module the inner edge 216 (the surface closest to the cushion) includes a notch 230 towards the front end thereof, which is adapted to receive the hook 208. The notch is positioned on the inner edge of the forearm channel in such a position that when the elbow is at about 90° flexion the notch is aligned with the hook and can engage with the hook. The hook may be made of the plastics material or any other appropriate material that can engage with the notch on the inner surface of the forearm channel.

There may be several hooks in different positions on the connection plate, so that the forearm can be extended by different degrees. Alternatively there may be several notches on the inner edge of the forearm module which engage with a single hook to enable the same variation in extension of the forearm.

It should be noted that the hook and notch may be located respectively on the inner edge of the forearm module and on the connection plate. In other words on the opposite surfaces to that described above. In this arrangement the hook would be pointing downwards rather than upwards to enable engagement with the corresponding notch.

It will be appreciated that different forms of locking device may be used instead of the notch and hook arrangement described herein.

In normal use of the brace, the hook is fixed into the notch to keep the elbow in the preferred 90° flexion position. However, when the patient wishes to extend their arm they simply need to disengage the hook from the notch to allow the forearm to extend. As the posterior upper arm support is not connected to the forearm module the upper arm does not move when the forearm is extended this ensures that the shoulder joint is maintained in its required position for healing.

In one embodiment, the hook and notch can the disengaged by slight contraction of the bicep muscle which causes the forearm channel to raise slightly relative to the cushion. This slight movements can disengage the hook from the notch and enable the patient to subsequently extend their arm to another position other than 90° flexion about the pivot point provided by pin 228. To return the arm to the 90° flexion position the patient need only lift their forearm with the other hand to re-engage the hook in the notch. The rigidity of the pivot point substantially prevents any movement of the forearm module in other directions than that intended by the pivot point itself.

Figure 4A:
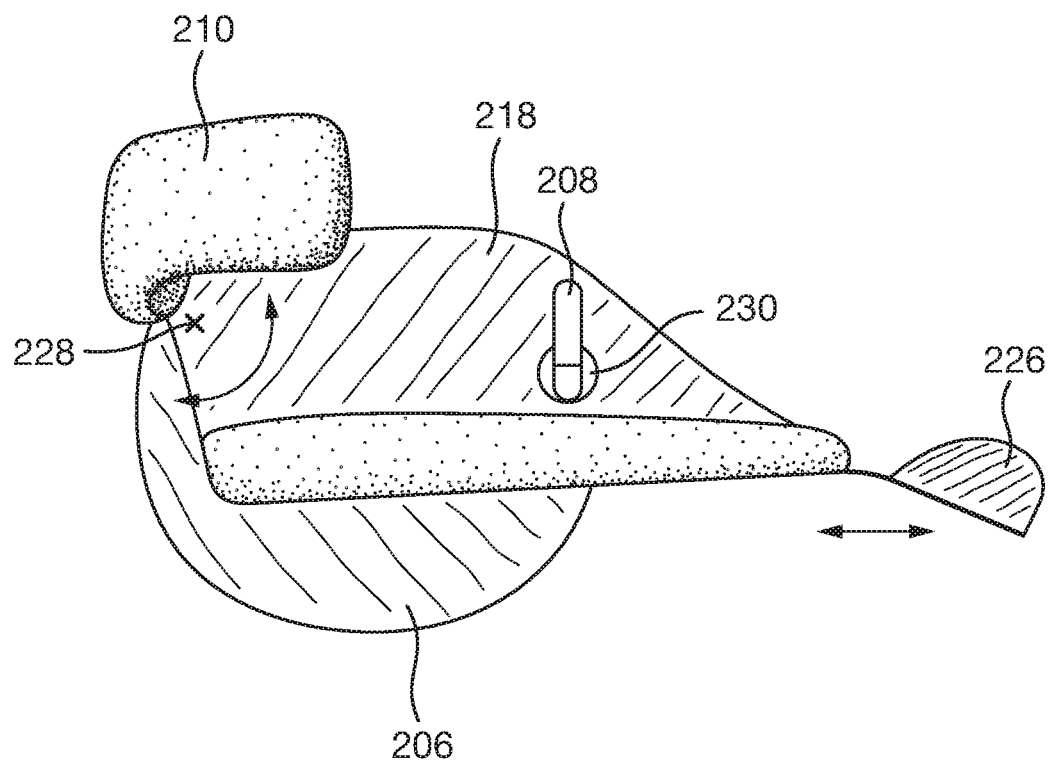
FIG. 4a is a more detailed schematic diagram of the elbow lock of FIG. 3 with the lock at about 90° flexion, in accordance with an aspect of the present invention.
Figure 4B:
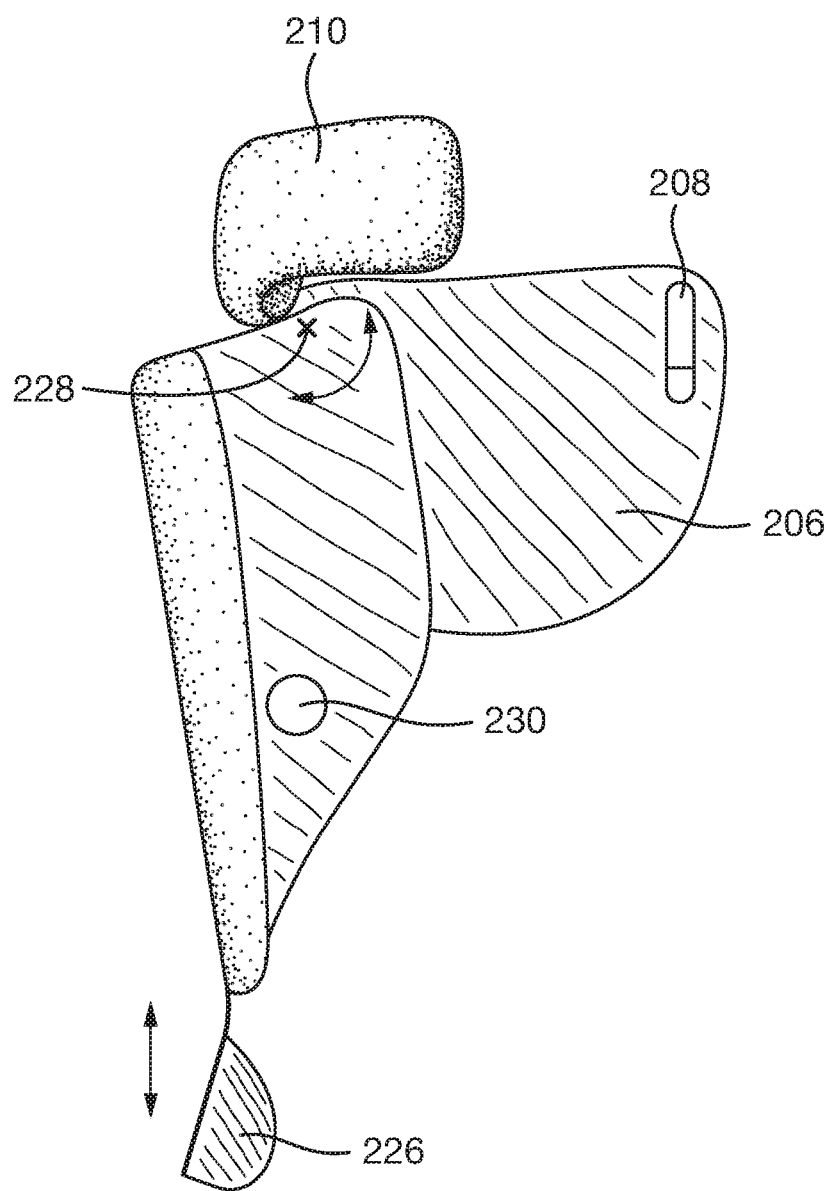
FIG. 4b is a more detailed schematic diagram of the elbow lock of FIG. 3 with the lock open, in accordance with an aspect of the present invention

FIGS. 4a and 4b show the brace in the position of the elbow at about 90° flexion and with the elbow extended respectively. In both diagrams the axis of rotation of the brace is shown. The axis of rotation forms a hinge between the link plate and forearm module at the rear end of the forearm channel. The hinge comprises a simple metallic pin 228 positioned facing the elbow joint which holds the link plate and the forearm module together at the rear and enables the forearm module to rotate relative to the pin when the hook and notch are disengaged. These figures also enable clear visibility of the hook and notch in both their engaged and disengaged positions.

Figure 5:
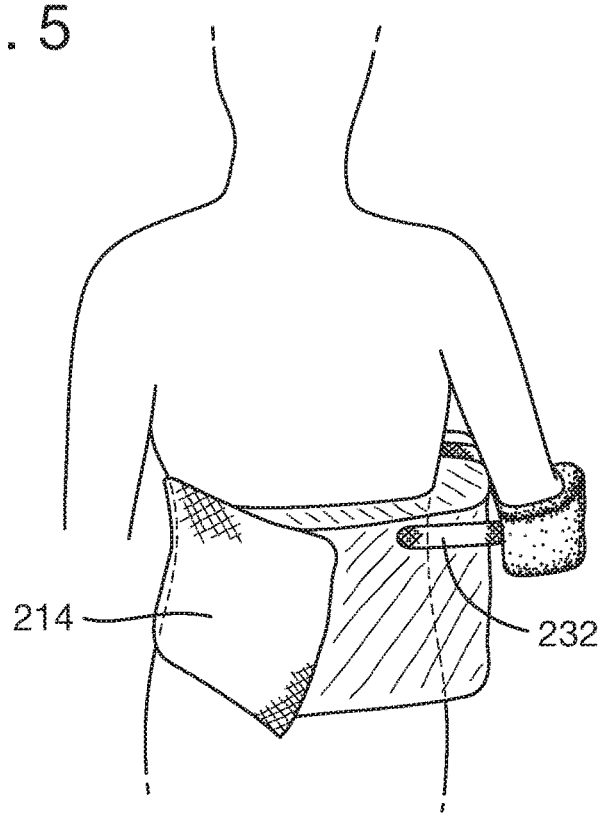
FIG. 5 is a schematic diagram of a rear view of the brace, in accordance with an aspect of the present invention.
Figure 6:
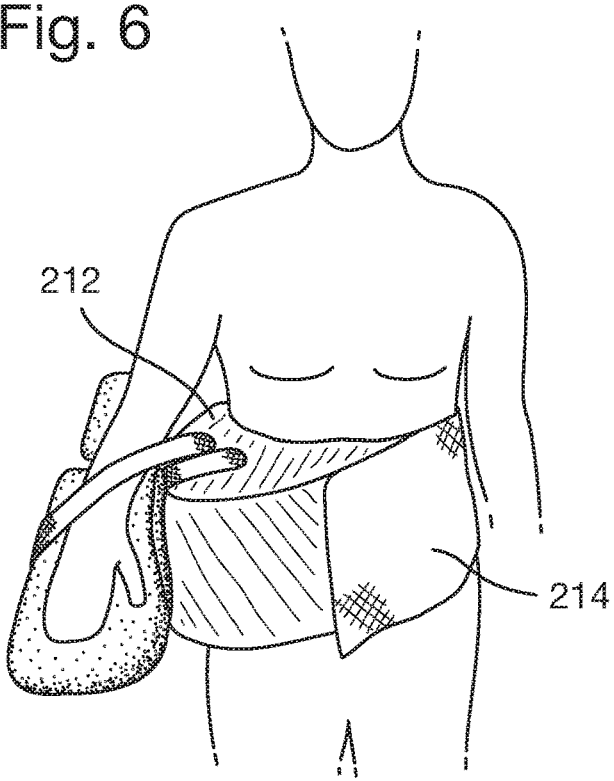
FIG. 6 is a schematic diagram of the front view the brace, in accordance with an aspect of the present invention.

FIG. 5 and FIG. 6 show respectively the rear and front views of the brace, in accordance with the present invention. In FIG. 5a the hook-and-loop support 232 is shown which is used to rigidly fix the forearm module to the trunk module. The posterior arm support is also rigidly connected to the connection plate to ensure the correct position of the upper arm in the brace. It should be noted the upper arm support can be fixed to other parts of brace as long as the upper arm is supported rigidly and is unable to move. An example of the shape of the cushion can be also seen in FIGS. 5 and 6.

The above described brace combines the required immobilization of various joints, such as the shoulder, elbow, and wrist. These joints are maintained in a rest position for a majority of the time but mobilization of certain joints is simple and autonomous thereby preventing stiffness and muscle and tendon problems.

The brace in accordance with the present invention provides a number of clear advantages over existing braces. The shoulder is immobilized in a position of neutral rotation and about 20° of abduction which corresponds to the rest position and the muscle tendon balance which gives the minimum tension to the cuff tendons and muscles. In the case of fractures of the proximal humerus the neutral position of rotation of the shoulder prevents malunion of the diaphysis and malunion of the tuberosity. In the case of anterior shoulder dislocation or reintegration of the anterior labrum, neutral rotation promotes healing in a good position on the anterior edge of the glenoid. In the case of repair of tendons in the rotator cuff, there is a perfect equilibrium between internal and external rotator cuff muscles, which is required to optimize the healing of the shoulder.

As the brace allows for elbow extension whilst the patient is either lying or standing muscle tendon retraction of the flexor muscles of the elbow is avoided thereby avoiding stiffness in the joint. The ability to extend the elbow a number of times during the day allows for the dispersion of any hematoma or post fracture or postsurgical edema. When the patient is lying down, the ability to extend the elbow means that sleeping is easier and the hand does not undergo unpleasant symptoms such as cooling, numbness and tingling.

When the patient is lying down elbow extension does not cause any movement of the shoulder, which protects osteosynthesis, re-insertions and tendon or ligament sutures. In addition, there is no pain generated by putting the soft tissue and bone fracture fragments under tension.

Mobilization of the elbow whilst the shoulder is not removed from the brace is possible. This allows for alternative postures and maximum output amplitude gain obtained after arthrolysis of the elbow. The ability to carry out a pendulum movement with the shoulder is not inhibited by the brace.

As the brace only uses a simple waist belt to hold the arm in position the patient can easily attach the brace autonomously without help from a third party. In addition, there are no complicated straps which can cause chafing and irritation and which are complex to put on even with help.

The brace includes an open channel for the forearm which means that there is support but not compression of the elbow and forearm. This has a number of advantages in terms of preventing unpleasant symptoms such as coldness in the forearm and hand, nerve tingling, and numbness.

The brace can be used in the treatment of a number of different conditions affecting the shoulder, elbow and/or wrist. These include:
a) Damage and/or reinsertion of tendons and soft tissue to the bone, for example rotator cuff or capsule in the shoulder; medial, lateral and cruciate ligaments in the elbow; and ligaments in the wrist and hand. It should be noted that for use with the elbow and or wrist the brace would typically be used to immobilize the joint for a first period of time, for example 2 to 3 weeks. Thereafter gradual reintroduction of movement of the elbow or wrist could be undertaken to aid the healing process and prevent the joint becoming unduly stiff.
b) Orthopedic treatment of fractures of the shoulder, elbow and wrist and also fractures of the humerus and/or forearm.
c) Surgical treatment of fractures of the shoulder, elbow, wrist, humerus and forearm; including the implantation of plates, pins nails, anatomical implants, prostheses et cetera.
d) Treatment of neurological pathologies such as monoplegia, hemiplegia or myopathy as well as the effects of paralysis of the brachial plexus.

In shoulder surgery the brace can be used post-operative preferably for any procedure, including but not limited to the following:
a) repair of the labral lesions;
b) SLAP (superior labral tear from anterior to posterior) lesions;
c) previous or subsequent dislocations;
d) repair of the rotator tendons;
e) total shoulder prosthesis;
f) fractures of the proximal humerus.

It will be appreciated that the above described brace may be adapted in numerous ways whilst still being within the scope of the present invention. Each element of the brace may be adapted, made of different materials, or orientated relative to one another in a different manner. All the various alternatives are intended to be included within the scope of the present invention.

What is claimed is:

1. A brace for supporting the forearm and for restricting movement of one of more joints, the brace comprising:
a trunk module attachable to a human body in a vicinity of a torso at a side of the body corresponding to an arm to be supported, wherein the trunk module includes a strap for attaching the brace to the body; and a first part of a locking mechanism;
a forearm module pivotable relative to the trunk module and adapted to support the forearm in a plurality of positions relative to an upper arm, the forearm module further including a second part of a locking mechanism capable of engaging and disengaging with said first part of the locking mechanism;
a posterior upper arm support attached to the brace in a fixed position to prevent movement of the upper arm and shoulder;
wherein in a first orientation the first part of the locking mechanism is engaged with the second part of the locking mechanism such that the forearm module is capable of positioning the forearm at a first position relative to the upper arm; and wherein in a second orientation the first part of the locking mechanism is disengaged from the second part of the locking mechanism such that the forearm module is capable of pivoting relative to the trunk module to enable the forearm to be positioned at a second position relative to the upper arm;
wherein the trunk module includes a connection plate on which one of the first or second part of the locking mechanism is located; and
a pivot joint pivotally connecting the connection plate and the forearm module to allow the forearm module to pivot relative to the trunk module.

2. The brace according to claim 1, wherein the first and second part of the locking mechanism comprise a hook engageable with a notch.

3. The brace according to claim 1, wherein the first position of the forearm relative to the upper arm is at an angle of about 90°.

4. The brace according to claim 1, wherein the second position of the forearm relative to the upper arm is at an angle between about 90° and about 180°.

5. The brace according to claim 1, wherein the trunk module further comprises a cushion for supporting the arm against the body at a particular lateral displacement, based on a thickness of the cushion.

6. The brace according to claim 1, wherein the trunk module further comprises an elasticated strap which passes around the body to hold the trunk module in the required position.

7. The brace according to claim 6, wherein the elasticated strap includes a fixing for securing the elasticated strap.

8. The brace according to claim 1, wherein the forearm module comprises a channel for supporting the forearm, wherein the channel includes an inner and outer edge and a curved-base portion.

9. The brace according to claim 8, wherein the inner edge of the channel is higher than the outer edge of the channel.

10. The brace according to claim 8, wherein one of the first or second part of the locking mechanism is located on the inner edge of the channel.

11. The brace according to claim 1, wherein said pivot joint includes a pivot pin.

12. The brace according to claim 1, further comprising more than one first and second parts of the locking mechanism to enable the forearm to be secured in intermediate positions between about 90° and about 180° on engagement of different first and second parts.

13. The brace according to claim 1 for allowing movement of at least one of the shoulder, elbow, wrist or forearm.

\* \* \* \* \*